(12) United States Patent
Burge et al.

(10) Patent No.: US 11,226,306 B2
(45) Date of Patent: Jan. 18, 2022

(54) MICROBIAL SENSOR SYSTEM FOR MONITORING AND IMAGING OF AN ENVIRONMENT

(71) Applicants: Scott R. Burge, Tempe, AZ (US); David A. Hoffman, Tempe, AZ (US)

(72) Inventors: Scott R. Burge, Tempe, AZ (US); David A. Hoffman, Tempe, AZ (US)

(73) Assignee: Burge Environmental. Inc., Tempe, AZ (US)

( * ) Notice: Subject to any disclaimer, the term of this patent is extended or adjusted under 35 U.S.C. 154(b) by 135 days.

(21) Appl. No.: 16/156,927

(22) Filed: Oct. 10, 2018

(65) Prior Publication Data

US 2019/0107509 A1  Apr. 11, 2019

Related U.S. Application Data

(60) Provisional application No. 62/715,965, filed on Aug. 8, 2018, provisional application No. 62/629,835, filed on Feb. 13, 2018, provisional application No. 62/616,589, filed on Jan. 12, 2018, provisional application No. 62/570,186, filed on Oct. 10, 2017.

(51) Int. Cl.
*G01N 27/416* (2006.01)
*G01N 27/327* (2006.01)
*G01N 27/30* (2006.01)
*A01G 7/00* (2006.01)
*G01N 33/487* (2006.01)
*G01N 33/24* (2006.01)

(52) U.S. Cl.
CPC ......... *G01N 27/4161* (2013.01); *A01G 7/00* (2013.01); *G01N 27/301* (2013.01); *G01N 27/3273* (2013.01); *G01N 33/24* (2013.01); *G01N 33/48707* (2013.01); *G01N 2033/245* (2013.01)

(58) Field of Classification Search
CPC .................. G01N 27/4164; G01N 27/301
See application file for complete search history.

(56) References Cited

U.S. PATENT DOCUMENTS 4,200,493 A * 4/1980 Wilkins ............... C12Q 1/04
204/403.01
5,254,461 A 10/1993 Rohrback et al.
(Continued)

OTHER PUBLICATIONS

W.R. Fischer, pH values and redox potentials in microsites of the rhizosphere, Zeitschrift fur Pflanzenernahrung und Bodenkunde 152(2), 1989, p. 191-95. (Year: 1989).*
(Continued)

*Primary Examiner* — Luan V Van
*Assistant Examiner* — Caitlyn Mingyun Sun
(74) *Attorney, Agent, or Firm* — Snell & Wilmer L.L.P.

(57) ABSTRACT

A microbial sensor, microbial sensing system, and method that can be used to determine the chemical environment of unsaturated soils, rhizosphere, and/or plants are disclosed. The microbial sensing system can be used for monitoring the health of plants including nutrients, salinity, contaminants, chemicals (pesticides, herbicides) and diseases. A microbial sensing system can include one or more indicator electrodes and a reference electrode. The microbial sensing system can include a signal acquisition and/or communication module to allow the real-time collection of data from field deployments and laboratory investigations.

14 Claims, 10 Drawing Sheets

(56) References Cited

U.S. PATENT DOCUMENTS

| | | | |
|---|---|---|---|
| 5,487,981 A | | 1/1996 | Nivens et al. |
| 5,639,956 A | * | 6/1997 | Christy .................. G01N 33/24 |
| | | | 73/19.01 |
| 6,113,762 A | | 9/2000 | Karube et al. |
| 9,299,999 B2 | | 3/2016 | Chang et al. |
| 10,113,990 B2 | | 10/2018 | Burge et al. |
| 2014/0237897 A1 | * | 8/2014 | Lotvak ..................... A01G 7/00 |
| | | | 47/62 R |
| 2016/0333387 A1 | * | 11/2016 | Turick ..................... C12Q 1/02 |
| 2017/0045470 A1 | * | 2/2017 | Burge ................ G01N 27/4035 |
| 2019/0011397 A1 | | 1/2019 | Burge et al. |
| 2019/0040351 A1 | | 2/2019 | Burge et al. |

OTHER PUBLICATIONS

R.D. Delaune, Redox Potential, Encyclopedia of Soils in the Environment, 2005, p. 366. (Year: 2005).*

A. Kaur, Anode modification to improve the performance of a microbial fuel cell volative fatty acid biosensor, Sensors and Actuators B 201, 2014, p. 266-273. (Year: 2014).*

USPTO; Requirement for Restriction dated May 3, 2018 in U.S. Appl. No. 15/237,230.

USPTO; Notice of Allowance dated Jul. 19, 2018 in U.S. Appl. No. 15/237,230.

USPTO; Notice of Allowance dated Aug. 24, 2018 in U.S. Appl. No. 15/237,230.

* cited by examiner

MICROBIAL SENSOR SYSTEM FOR MONITORING AND IMAGING OF AN ENVIRONMENT

CROSS-REFERENCE TO RELATED APPLICATIONS

This application claims the benefit of U.S. Provisional Application No. 62/570,186, filed Oct. 10, 2017, and entitled "Microbial Sensor System for Monitoring the Rhizosphere and Adjacent Soils," U.S. Provisional Application No. 62/629,835, filed Feb. 13, 2018, and entitled "Microbial Sensor System for Bioimaging the Rhizosphere," U.S. Provisional Application No. 62/616,589, filed Jan. 12, 2018, and entitled "Microbial Sensor System for Monitoring the Subsurface," and U.S. Provisional Application No. 62/715,965, filed Aug. 8, 2018, and entitled "Anaerobic Reference Cell for Microbial Monitoring System." The contents of the above provisional applications are incorporated herein by reference to the extent such contents do not conflict with the present disclosure.

STATEMENT REGARDING FEDERALLY-SPONSORED RESEARCH OR DEVELOPMENT

This invention was made with government support by the Office of Science grant numbers DE-FOA-0001405 and DE-SC0018495 awarded by the Department of Energy. The government has certain rights in the invention.

FIELD OF THE INVENTION

The present disclosure generally relates to sensors and systems, and to methods of using the sensors and systems. Exemplary embodiments of present disclosure relate to sensors and systems that employ open-circuit voltage and/or recovery voltage measurements to provide information concerning biochemical characteristics, such as microbial activity, reduction/oxidation conditions, and/or substrate concentrations of an environment, such as saturated or unsaturated soil environments, plant tissues, and the like.

BACKGROUND OF THE DISCLOSURE

Microbial fuel cell technology was developed primarily for the conversion of waste products (sewage, farming wastes, etc.) into energy. Recently, the use of microbial fuel cells as sensors has been developed. For example, Burge et al. in U.S. patent application Ser. No. 15/237,230, dated Aug. 15, 2016, and U.S. patent application Ser. No. 16/054,789, dated Aug. 3, 2018, disclosed microbial sensor systems using open-circuit voltage and recovery voltage as a metric for determining biochemical conditions and substrate concentrations in aqueous and saturated environments.

However, such sensors are generally not suitable for monitoring soils (saturated and unsaturated), such as soils adjacent to the roots of plants (rhizosphere) or for the investigation of contaminated soils and sediments. Further, such systems are generally not suitable for directly measuring biochemical characteristics of plants. Accordingly, improved sensors, sensor systems, and techniques for using the sensors and sensor systems are desired.

SUMMARY OF THE DISCLOSURE

Various embodiments of the present disclosure relate to methods and systems for characterizing natural and contaminated saturated and unsaturated environments, such as soils (such as soils adjacent to the roots of plants (rhizosphere)), sediments, and plants. For example, various embodiments can be used to monitor natural attenuation and/or active remedial actions. While the ways in which various embodiments of the disclosure address the drawbacks of the prior art are discussed in more detail below, in general, the disclosure provides systems and methods for monitoring of, for example, rhizosphere and plant tissue to investigate impacts of chemicals, moisture, temperature, microbial compositions, plant diseases and other biochemical characteristics. The systems may be used to determine the health of plants by direct measurement of the internal and/or external tissues of plants. Other applications of systems and methods described herein include investigations of the impacts of climate change on the health of plants, soils and microbial communities.

In accordance with exemplary embodiments of the disclosure, a microbial sensing system includes an indicator electrode; a reference electrode; and a signal acquisition module electrically coupled to the indicator electrode and the reference electrode, wherein the signal acquisition module comprises measurement circuitry that comprise a high-impedance potentiometer, having an impedance greater than or equal to 10 megaohms. The impedance of the impedance potentiometer may be greater than 100 megaohms. In accordance with other examples, the impedance can range from about 10 megaohms to about 50 teraohms, or about 100 megaohms to about 50 teraohms, or 10 megaohms to about 500 gigaohms, or about 100 megaohms to about 1 gigaohm. In accordance with various aspects of these embodiments, the indicator electrode comprises a material selected from the group consisting of graphite, gold, platinum, titanium, and carbon fabrics. The microbial sensing system can also include a communication module comprising circuitry to transmit data to a remote device. Additionally or alternatively, the microbial sensing system can include a data logger. The reference electrode can be or include standard electrode, a cathode, or another/second indicator electrode (e.g., in a static environment). Exemplary microbial sensing systems can include one or more indicator electrodes and/or reference electrodes. For example, a microbial sensing system can include a plurality of indictor electrodes and a single reference electrode. In accordance with further aspects of these embodiments, the microbial sensing system can measure an open circuit voltage between the indicator electrode and the reference electrode and/or a recovery voltage between the indicator electrode and the reference electrode.

In accordance with further exemplary embodiments of the disclosure, a method of measuring biochemical characteristics in soil includes placing an indicator electrode in soil, allowing a biofilm to form over at least a portion of the indicator electrode, and measuring a potential difference between the indicator electrode and a reference electrode using a high-impedance potentiometer. The biochemical characteristics can be any of the biochemical characteristics described herein, such as chemicals (composition and/or concentrations), moisture content, temperature, microbial compositions and/or concentrations, plant diseases, and the like. In accordance with various aspects of these embodiments, an indicator electrode is placed within a rhizosphere. Additionally or alternatively, an indicator electrode can contact a plant (internal and/or external parts). The reference electrode can include any of the reference electrodes described herein. The method of measuring biochemical characteristics can further include a step of providing current between the indicator electrode and the reference electrode before a step of measuring the potential difference. Although described above in the context of soil, methods in accordance with the present disclosure can include measuring plant characteristics and/or characteristics of sediments.

As set forth in more detail below various specific examples of the disclosure provide (1) a system and method for microbial monitoring of soils and other unsaturated zones using a cathode as a reference electrode; (2) a system and method for microbial monitoring of soils and other unsaturated zones using an electrode located in a stable or static environment, such as an anaerobic soil zone or an artificially-created constant (static) anaerobic environment, as the reference electrode; (3) a system and method for microbial monitoring of soils, sediments, saturated zones, and aqueous environments using an artificially-created anaerobic cell; (4) a system and method for microbial monitoring of a rhizosphere and surrounding soils using independent indicator electrodes and a reference electrode; (5) a system and method for microbial monitoring of a rhizosphere, surrounding soils and/or tissues of the plants (e.g., roots, stem, leaves) using independent indicator electrodes and a reference electrode; (6) a system and method for microbial monitoring of an (e.g., unsaturated) environment, where the indicator electrodes and reference electrode are incorporated into a probe; (7) a system and method for microbial monitoring that includes use of the sensor probes and an independent reference electrode; (8) a system and method for microbial monitoring system including one or more probes, one or more reference electrodes and one or more signal acquisition and/or communication modules; (9) a system and method for microbial monitoring using sensors coated with nutrients and/or other chemicals to alter the microbial communities populating the surface of the indicator sensors; and (10) a system and method for microbial monitoring using sensors coated with nutrients and/or other chemicals to alter the microbial communities populating the surface of the sensors and an embedded data acquisition/data communication circuit.

BRIEF DESCRIPTION OF THE DRAWING FIGURES

A more complete understanding of exemplary embodiments of the present disclosure may be derived by referring to the detailed description and claims when considered in connection with the following illustrative figures.

Figure 1:
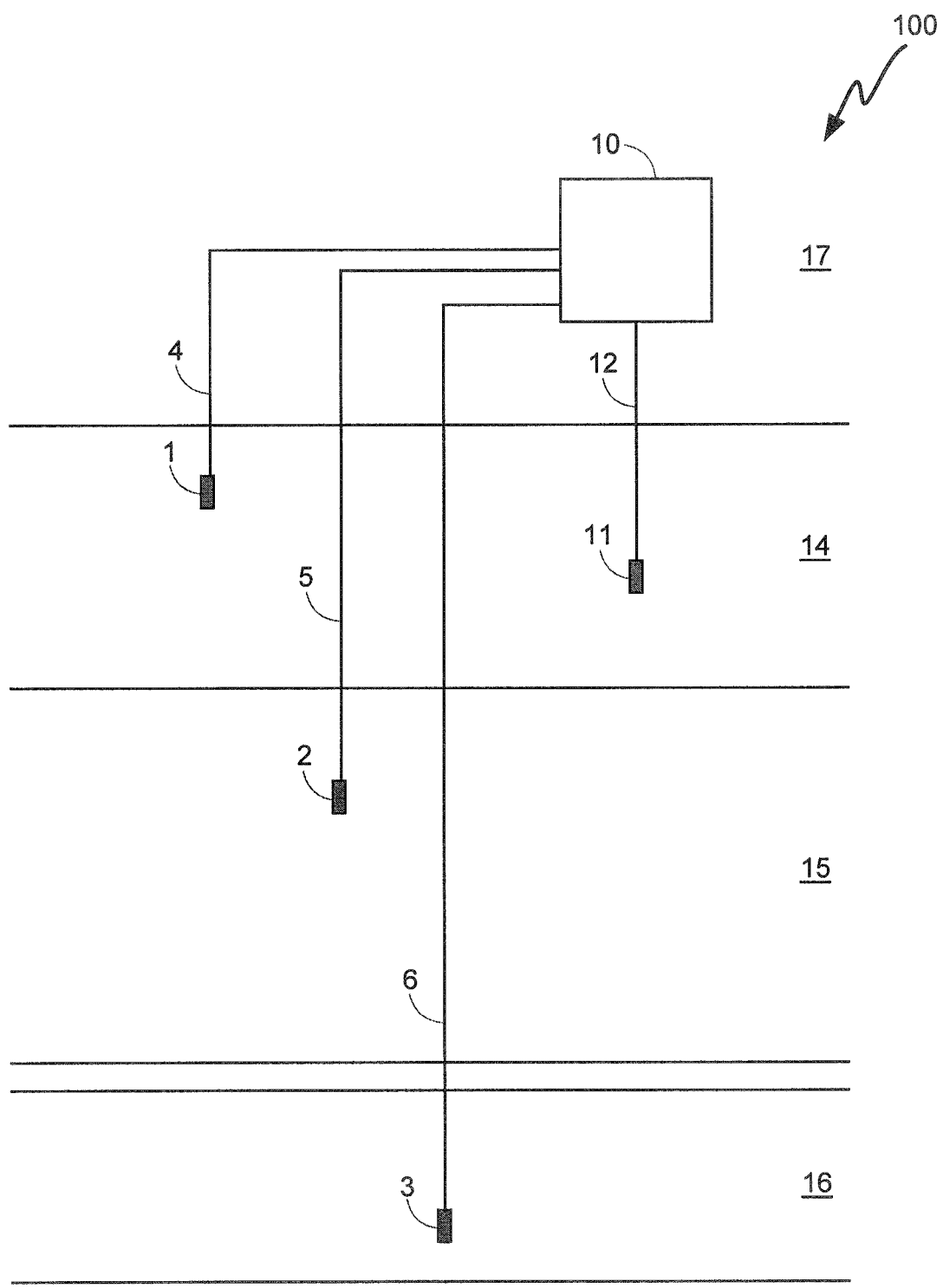
FIG. 1 illustrates a microbial sensing system for monitoring soil conditions using one reference electrode (cathode) and multiple indicator electrodes (anodes) in accordance with at least one embodiment of the disclosure.

It will be appreciated that elements in the figures are illustrated for simplicity and clarity and have not necessarily been drawn to scale. For example, the dimensions of some of the elements in the figures may be exaggerated relative to other elements to help to improve understanding of illustrated embodiments of the present disclosure.

DETAILED DESCRIPTION OF EXEMPLARY EMBODIMENTS OF THE DISCLOSURE

The description of exemplary embodiments of methods, systems, and probes provided below is merely exemplary and is intended for purposes of illustration only; the following description is not intended to limit the scope of the disclosure or the claims. Moreover, recitation of multiple embodiments having stated features is not intended to exclude other embodiments having additional features or other embodiments incorporating different combinations of the stated features.

As noted above, prior microbial sensor technologies (energy production, bioremediation, analytical sensors) are primarily based on the measurement of electrical current between an anode and a cathode. The measurement of constant current allows for the determination of substrate concentration in a solution. In contrast, the inventors surprisingly found that measurements of open-circuit voltage (OCV) and/or recovery voltage (RV) are capable of providing information distinct from the measurement of constant current and can use less sensitive instrumentation to provide meaningful information regarding substrates and concentrations thereof that are or may be present in an environment. Further, unlike typical sensor technologies, methods and systems described herein can be used to monitor and/or characterize unsaturated systems, such as plants and soils.

Microbial Sensing System

Exemplary microbial sensing systems as described herein are electrochemical analytical systems that include: 1) one or more indicator electrodes, and 2) at least one reference electrode. The indicator and reference electrodes are electrically connected to a signal acquisition board or module. The signal acquisition module includes one or more high-impedance potentiometers and circuitry to collect microbial potentiometric and/or kinetic signals. The impedance of the impedance potentiometer may be greater than 100 megaohms. In accordance with other examples, the impedance can range from about 10 megaohms to about 50 teraohms, or about 100 megaohms to about 50 teraohms, or 10 megaohms to about 500 gigaohms, or about 100 megaohms to about 1 gigaohm. The data from the signal acquisition module can be transmitted (e.g., using the same or another module—e.g., a communication module) to a remote user device, such as a computer, phone, tablet, or the like, using telemetry, satellite and/or cellular transmission. Additionally or alternatively, the data can be stored on a data logger— e.g., integrated with or located near the signal acquisition module. In this disclosure, the term module may be used to refer to a physical circuit, a collection of hardware components, a logical module, firmware, software (applications, functions, subroutines, etc.), functional module, and/or a combination of the above.

Indicator Electrodes

The indicator electrode can be formed of graphite. Other inert materials can be used to form the indicator electrode, including gold, platinum, titanium, carbon fabrics and other non-oxidizable materials. The surface of the indicator electrode, after insertion in the soil, can become populated with a biofilm. The biofilm populating the surface of the indicator electrode oxidizes substrates in the soil profile or other media. The oxidation of the substrates creates a difference in electrochemical potential between the indicator electrode(s) and the reference electrode. The difference in the potential is measured by a high-impedance potentiometer (e.g., having an impedance as set forth herein). The indicator electrode can be deployed within the soil profile or at the surface of the soils (saturated or unsaturated). If a rhizosphere is being investigated, an indicator electrode may be directly connected to a plant under investigation. The indicator electrode may be attached (internally or externally) to various parts of a plant, including roots, stems and leaves.

Reference Electrodes

Suitable reference electrodes for use with various embodiments and examples of the disclosure include standard electrodes (e.g., silver/silver chloride or calomel), a cathode, and/or another/second indicator electrode placed in constant, unchanging (i.e., static) environmental conditions. An indicator electrode may be used as a reference electrode if the potential of the electrode does not significantly change over time. Three examples of where an indicator electrode does not significantly change in potential over time include: 1) an indicator electrode placed in a constant, anaerobic soil zone, 2) an indicator electrode placed into an artificially-created constant, anaerobic environment, and 3) an indicator electrode placed near or at the surface of the soils, where the electrode is exposed to oxygen. Standard electrodes and indicator electrodes may be used where only potentiometric measurements are collected using a high-impedance potentiometer. If current is passed between the indicator (anode) electrode and reference electrode, a cathode is typically used. A current is passed during the kinetic measurements (e.g., when a recovery voltage is measured). A cathode may be used as reference for both potentiometric and kinetic measurements. Several designs of cathodes and anodes are disclosed in U.S. patent application Ser. No. 15/237,230, entitled MICROBIAL SENSOR SYSTEM FOR THE ASSESSMENT OF SUBSURFACE ENVIRONMENTS and filed Aug. 15, 2016 and U.S. patent application Ser. No. 16/054,789, entitled ELECTROCHEMICAL MICROBIAL SENSOR SYSTEM AND METHOD OF USING SAME and filed Aug. 3, 2018, the contents of which, to the extend such contents do not conflict with the present disclosure, are hereby incorporated herein by reference. Alternatively, the cathode may be located on the surface, or slightly below a (e.g., soil or sediment) surface to allow the introduction of atmospheric oxygen to the cathode. A cathode in accordance with the disclosure includes an inert, non-oxidizable material, such as carbon, graphite, or metal (e.g., Au, Pt, Ti), which can be exposed to atmospheric oxygen. The surface of the non-oxidizable material, such as carbon fabric, can be covered with a material, such as platinum, to catalyze the reduction of atmospheric oxygen. In most field and laboratory applications, the surface of the cathode, after insertion in saturated or unsaturated soils, becomes populated with a biofilm, allowing bacteria enzymes to serve as the catalyst for the reduction of oxygen. The population of the surface of the cathode with a biofilm is referred to as a biocathode.

The use of multiple indictor electrodes (e.g., anodes) with one reference electrode (e.g., standard cell, cathode, or indicator electrode in a static environment) can be used, when, for example, the microbial sensing system is operated in either the open-circuit voltage (OCV) or kinetic modes of operation. OCV mode of operation measures a voltage between an indicator electrode and a reference electrode with no measureable current passing between the indicator and reference electrodes. The kinetic mode of operation initially flows a current between an indicator electrode (e.g., an anode) and a reference electrode (e.g., a cathode) for a brief period of time (several seconds to minutes) and then observing the recovery voltage (OCV) between the anode and cathode after the flow of current is terminated. A more detailed explanation is detailed in U.S. patent application Ser. No. 15/237,230.

Differences between using a standard cell (e.g., silver/silver chloride or calomel) versus a cathode as a reference cell include: 1) the ultimate electron acceptor of the two technologies, and 2) transfer of ions (i.e., liquid junction) of the two technologies. In accordance with various embodiments of the disclosure, for a cathode, the ultimate electron acceptor is atmospheric oxygen. After the oxygen accepts the electron, the cathode is not negatively impacted by the transfer of the electron. If a standard cell, for instance silver/silver chloride, accepts an electron, a silver ion is reduced to silver. Therefore, passing currents to the standard cell has an impact of the cell by changing the internal chemistry of the cell. Thus, a cathode has no long-term consequences of accepting electrons through electrical currents; however, passing currents to a standard cell may negatively impact the performance on the cell. Because of this, a cathode is typically used when the microbial sensing system is operated in the kinetic mode. Either a standard cell or cathode may be used when the microbial sensing system is operated in a potentiometric/OCV mode of operation.

A difference between a standard cell and cathode is the requirement of a liquid junction. Standard cells (e.g., silver/silver chloride and calomel) use metal ions in association with a salt of the metal in a solution (or paste) to create a potential of known voltage. The reference cell transfers ions to the solution under investigation. The transfer mechanism is known as a salt bridge or liquid junction. This junction is designed to be placed into a solution being investigated. If an unsaturated zone is being investigated, the performance of the liquid junction is greatly diminished. However, a cathode is typically fabricated from a carbon cloth and no solution is required for its operation. The cloth can be placed into an unsaturated zone and the cloth readily accepts electrons from an anode and exchanges ions with the unsaturated environment with no requirement for a solution to be present. This unique ability of the cathode allows its use as a reference cell in unsaturated environments.

The reference electrode may be placed into either the unsaturated soil profile or into the saturated zone below the unsaturated soil profile. Because the standard electrodes (Ag/AgCl and calomel electrodes) typically have a liquid junction, these reference cells perform best in saturated zones. The cathodes or additional/second indicator electrodes exposed to oxygen may be used in unsaturated zones.

Another type of reference cell is created by attaching a non-oxidizing material (e.g., graphite, carbon cloth, graphene, Pt, Ti, Au) on an internal or external location (e.g., leaf, stem, and/or root) of a plant. An electrode connected to a plant will vary over time; however, the plant as the point of reference can be useful in rhizosphere investigations.

Signal Acquisition/Communication Module(s)

The signal acquisition and communication module(s) are designed to acquire data from the indicator and reference electrodes and to store and/or transmit the data to remote user devices. Exemplary signal acquisition modules can acquire potentiometric (open-circuit voltage) and/or kinetic (recovery voltage) signals from the indicator and reference electrodes.

Potentiometric signals are the open-circuit voltages (OCV) measured between a reference electrode and each of the indicator electrodes. The voltage is measured by high-impedance potentiometers (e.g., >10 megaohms for saturated environments and >100 megaohms for dry soils, or other impedance values as described herein. Potentiometric signals are typically used to determine biochemical characteristics (e.g., potentiometric signal correlates with reduction-oxidation, dissolved oxygen, total dissolved carbon, and other biochemical characteristics) of a soil, rhizosphere, and/or plant under investigation.

As briefly noted above, kinetic signals are generated by a two-step process. The process is outlined in greater detail in U.S. patent application Ser. No. 15/237,230. The first step includes electrically connecting an indicator electrode (e.g., anode) with a reference electrode (e.g., cathode) to allow a discharge the electrons stored in temporary electron acceptors (e.g., cytochromes, and the like) of a biofilm populating a surface of the indicator electrode. During the second step, the flow of electrons between the indicator electrode and the cathode is terminated. After the flow of electrons is terminated, the electrical potential between the anode and cathode increases over time. The signal acquisition module uses a high-impedance potentiometer, e.g., having an impedance as noted herein, to measure the increase of electrical potential (referred to herein as recovery voltage) versus time. The kinetic signal can be used to determine substrate concentration, rate of substrate conversion, metabolic gas production, and the like.

The electrical signals generated by the signal acquisition module are transmitted to a remote user through an integrated or separate communication module, which can include including Bluetooth® transmission circuits and protocols, radio telemetry circuits and protocols, cellular and/or satellite modems, or the like. For example, a cellular modem can be used to transmit the data from the signal acquisition or communication module to cloud-based databases for storage and retrieval of the data by the users. The data can be retrieved using, for example, open-source dashboards and data visualization websites.

Additionally or alternatively, the data may be stored on a data logger located on or adjacent to the signal acquisition module of, for example, field-deployable systems. In these cases, a user may physically retrieve the data from the data logger by electrically connecting (or using short-range communication protocols) another device to the data logger or system.

Applications of the Data Collected for Field-Deployable or Laboratory-Based Systems Exemplary microbial sensing systems as described herein allow collection of real-time data and/or data collected at programmable time intervals (e.g., every 30 minutes, every hour, every day, or the like). The data collected from the microbial sensing system can be used to investigate the impacts of chemicals (e.g., fertilizers, pesticides, herbicides, contaminants, and/or salinity), moisture, temperature, microbial composition, plant diseases and other biochemical characteristics related to the health of plants. The data may be used to increase the yield of agricultural plants. Additionally or alternatively, the data can be used to determine the effectiveness of a remedial action of contaminated sites.

Because, in accordance with various examples of the disclosure, either reference and/or indicator electrodes can be connected to the interior or exterior surfaces of plants, exemplary microbial sensing systems can be used to investigate the impact of the biochemical characteristics, such as chemicals, moisture, temperature, microbial composition, diseases and the like impacting the health of plants within the plant under investigation. Thus, exemplary microbial monitoring systems have can be used to investigate the subsurface conditions impacting plants (rhizosphere) and/or plant tissues (external and internal).

SPECIFIC EXAMPLES

The examples provided below are merely exemplary, and are not meant to limit the scope of the invention. Further, unless stated otherwise, it will be appreciated that various components of one example can be interchanged with the same or similar components of another example.

Example 1

Referring to FIG. 1, a microbial sensing system 100 that includes a reference electrode comprising a cathode 11 positioned within or at the surface of a soil zone 14 in a location where the cathode 11 is exposed to the atmosphere 17, is illustrated. The cathode 11 connects to a cathode cable 12 that connects to a signal acquisition module 10. The cathode 11 may include or be composed of, for example, carbon fabric, graphite, graphene, and/or other non-oxidizable material or metals (e.g., Au, Ti, Pt).

In the illustrated example, microbial sensing system 100 includes one or more indicator electrodes 1, 2, 3 placed at various vertical and horizontal locations within an environment (e.g., soil or sediment), allowing the characterization of a soil/sediment profile of various environment locations 14, 15, 16. Each of the indicator electrodes 1, 2, 3 can be connected to a corresponding indicator cable 4, 5, 6. The indicator cables 4, 5, 6 connect the respective indicator electrode 1, 2, 3, to signal acquisition module 10. The signal acquisition module 10 includes high-impedance potentiometers, e.g., having an impedance as noted above, to measure the OCV between each of the indicator electrodes 1, 2, 3 and the reference electrode (cathode) 11. The measurement circuitry 10 and/or microbial sensing system 100 can incorporate a communication module, allowing the data to be transmitted to an off-site user device, such as a computer, phone, tablet or the like. Additionally or alternatively, the signal acquisition module 10 or the microbial sensing system 100 can include a data logger.

Example 2

Figure 2:
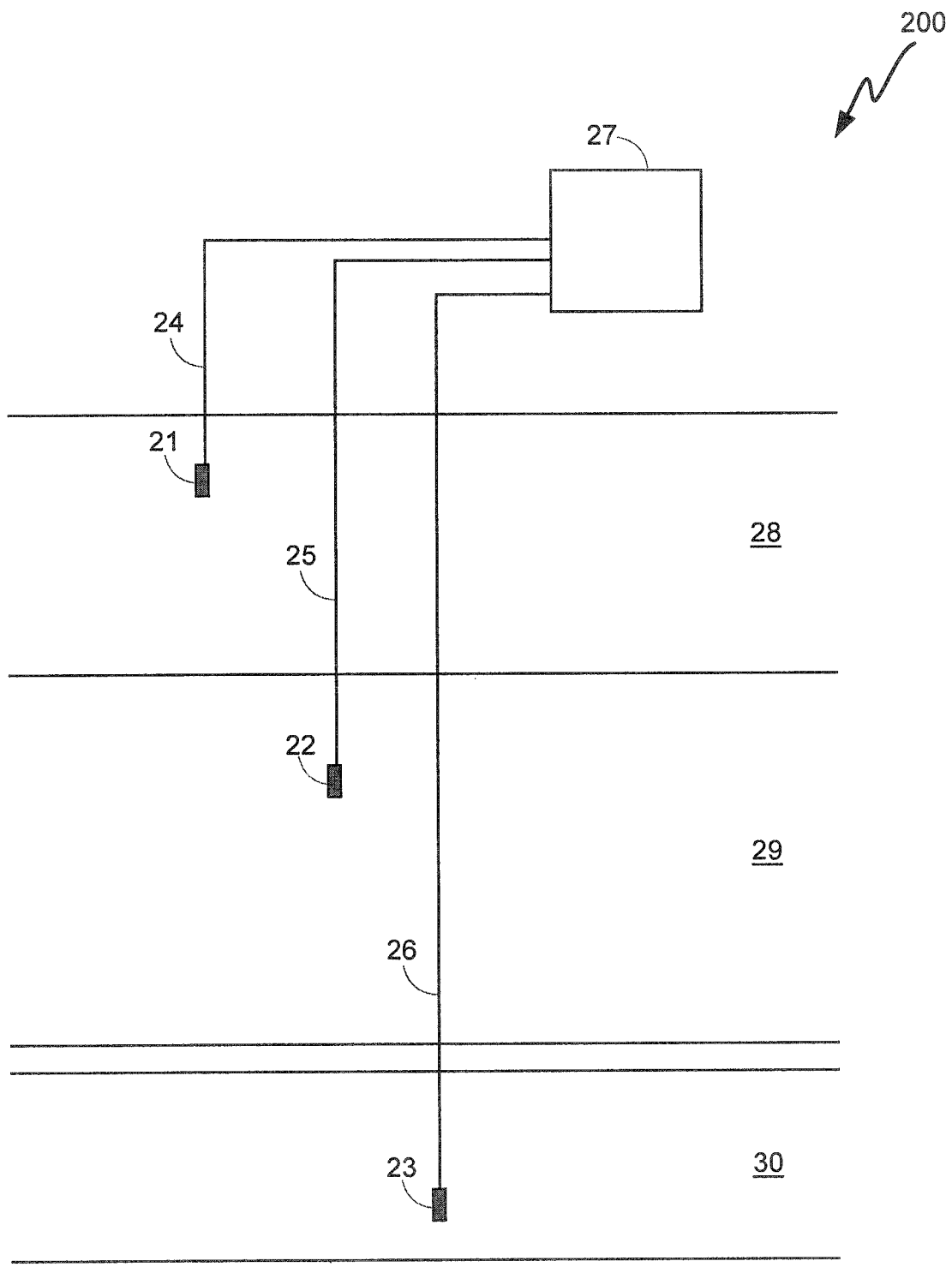
FIG. 2 illustrates a microbial sensing system for monitoring soil conditions with multiple indicator electrodes and using one of the indicator electrodes located in a static environment as the reference electrode in accordance with at least one embodiment of the disclosure.

Referring to FIG. 2, a microbial sensing system 200 that includes an electrode 23 placed within a constant, anaerobic (static) environment 30 is illustrated. If the anaerobic environment 30 has conditions that do not significantly vary over time (i.e., static), the indicator electrode 23 may be used as the reference electrode. The reference electrode 23 connects to an acquisition module 27 (which can be the same or similar to acquisition module 10) with a reference cable 26.

Multiple indicator electrodes 21, 22 are placed within various vertical and horizontal locations allowing the characterization of soil zones 28, 29, 30. Each of the indicator electrodes 21, 22 connects to a corresponding indicator cable 24, 25. The indicator cables 24, 25 connect to acquisition module 27. The acquisition module 27 employs high-impedance potentiometers, such as those described herein, to measure the OCV between each of the indicator electrodes 21, 22 and the reference electrode 23. The acquisition module 27 or microbial sensing system 200 can include a communication module, allowing the data to be transmitted from acquisition module 27 to an off-site device. Additionally or alternatively, the acquisition module 27 or microbial sensing system 200 may include a data logger.

Example 3

Figure 3:
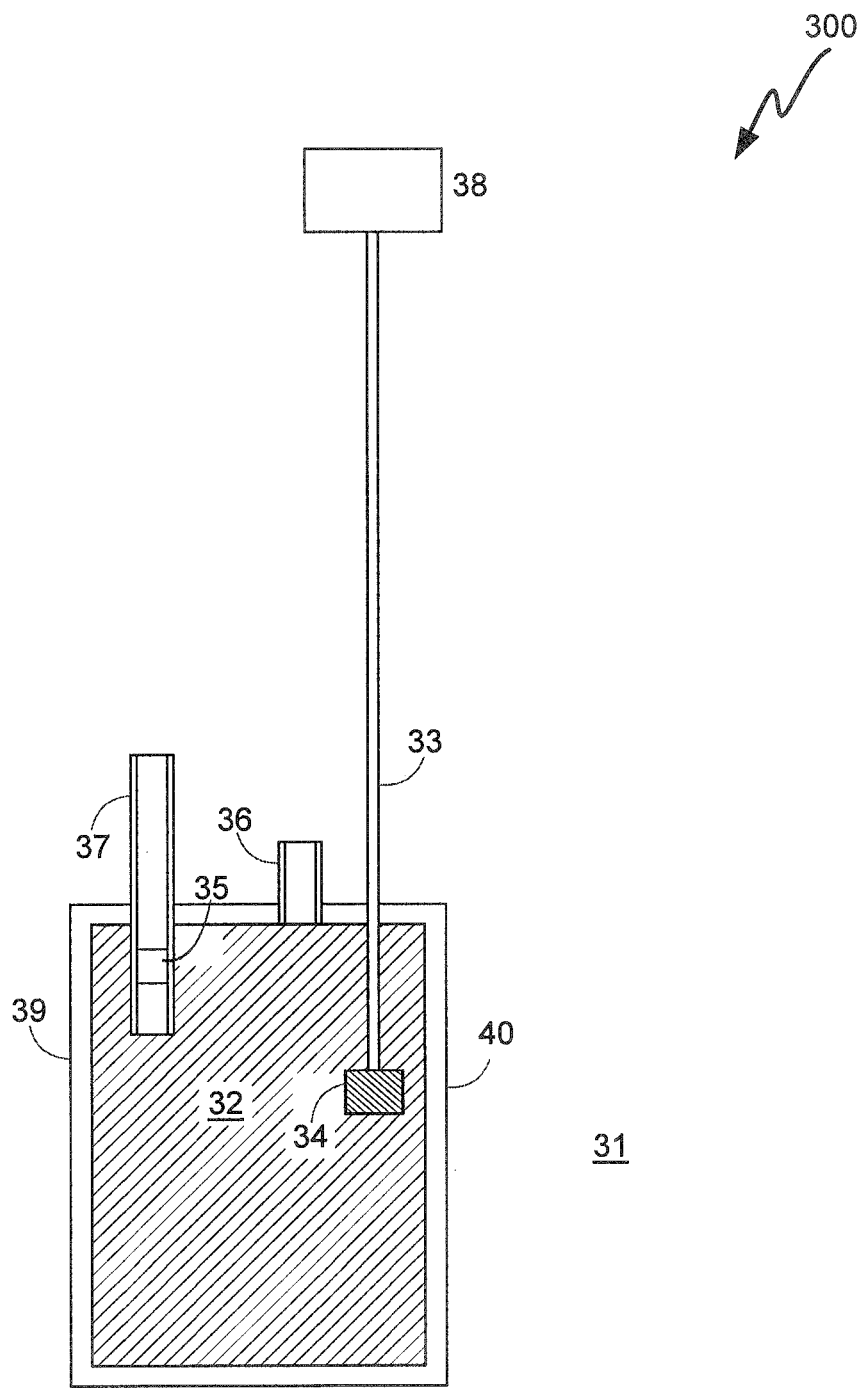
FIG. 3 illustrates a reference electrode with a static environment for investigation of saturated and unsaturated environments in accordance with at least one embodiment of the disclosure.

FIG. 3 illustrates another microbial sensing system 300 in accordance with various embodiments of the disclosure. Microbial sensing system 300 includes an artificially-created, anaerobic environment 32 that can be used as a reference electrode. In the illustrated example, a polymer cell 40 encloses anaerobic environment 32 from the surrounding environment 31. Alternatively, the anaerobic environment 32 can be collected from soils on the site, other locations with anaerobic soils, or created in a laboratory. An electrode 34 is located within the polymer cell 40. The electrode 34 may be fabricated from graphite, carbon fabric, or non-oxidable material or metals (Au, Ti, Pt). The electrode 34 electrically connects to an insulated electrical cable 33. The insulated electrical cable conducts the electrical signal (OCV) to a signal acquisition module 38. The components of the signal acquisition module 38 include a high-impedance potentiometer—e.g., as described herein. An orifice 37 is located within a wall 39 of the polymer cell 40. The orifice 37 allows the transfer of ions between the anaerobic environment 32 within the interior of the polymer cell 40 and the surrounding environment 31. By way of example, a diameter of the orifice 37 can be about 0.5 mm to about 3 mm and can be optimized to minimize the transfer of the ions between the interior and exterior of the polymer cell 40. The orifice 37 may be fitted with a frit 35 to regulate and optimize the transfer of ions. The frit 35 is optional. A gas tube 36 allows the venting of metabolic gases (e.g., methane, carbon dioxide) produced by the anaerobic environment 32 within the polymer cell 40. The gas tube 36 is optional.

Polymer cell 40 can be located within either aqueous zones (e.g., ground water or saturated sediments) or unsaturated soils. After anaerobic conditions are established within the polymer cell 40, the OCV potential of the electrode 34 can be used to determine the potentials of indicator electrodes located within saturated zones, unsaturated zones and/or plants being investigated.

Example 4

Figure 4:
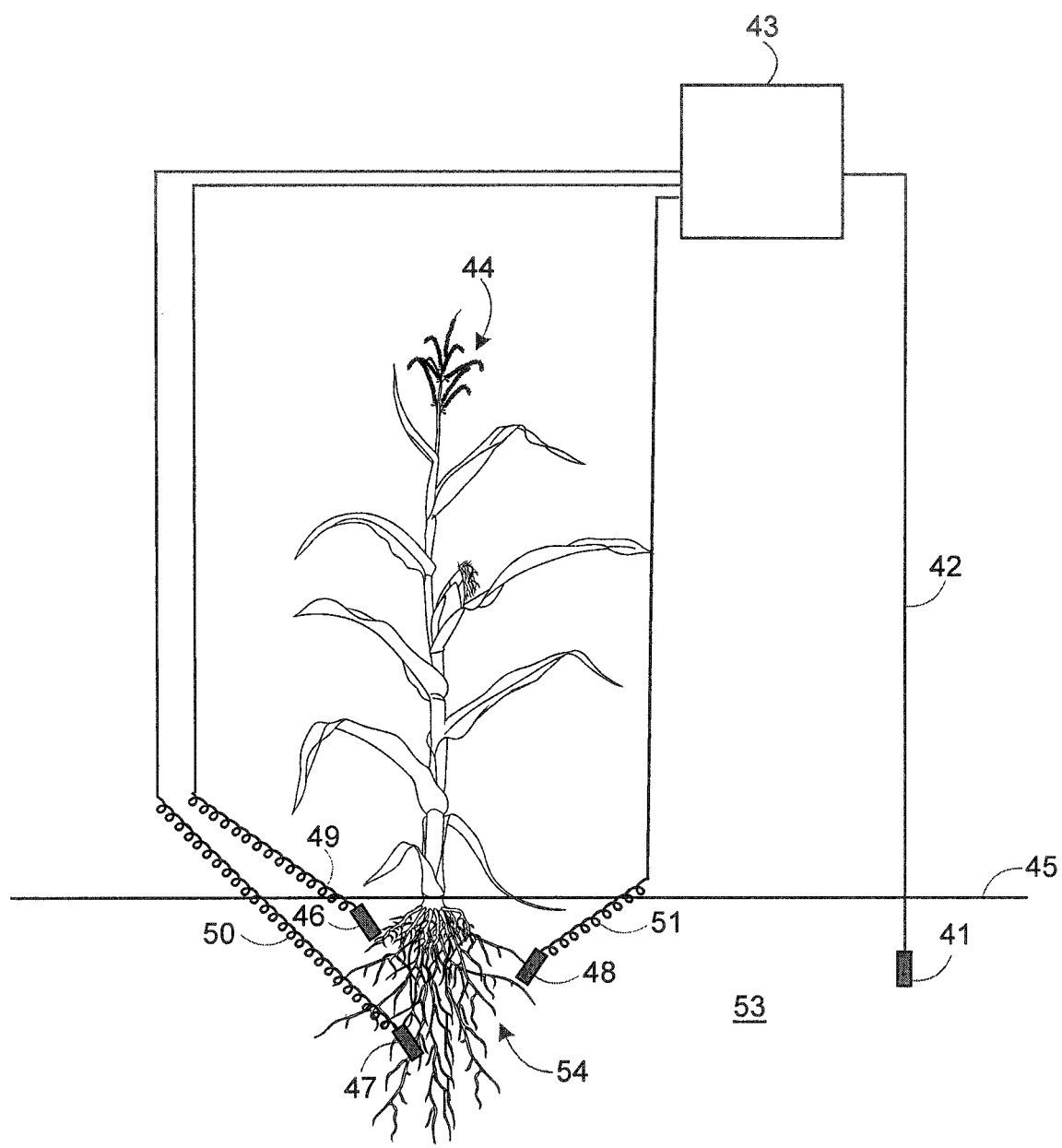
FIG. 4 illustrates a sensor system for monitoring soil conditions adjacent to a root system (rhizosphere) of a plant in accordance with at least one embodiment of the disclosure.

FIG. 4 illustrates another exemplary microbial sensing system 400 in accordance with the present disclosure. Microbial sensing system 400 can be used to monitor a subsurface soil 53 and the soils adjacent to a root system 54 (rhizosphere) of a plant 44. A cathode 41 is positioned on or near the surface 45, or in the subsurface of the soils 53. The location of the cathode 41 desirably allows for the exposure of atmospheric oxygen to the surface of the cathode 41. The cathode 41 is connected to an acquisition module 43 by a cathode cable 42. The cathode 41 serves as the reference electrode in this example. Additionally or alternatively, other reference cells, such as those described above in connection with examples 2 and 3 may be used in accordance with this example.

Multiple indicator electrodes 46, 47, 48 are placed at various vertical and horizontal locations adjacent to the root system 54 to characterize the soil 53 adjacent to the root system 54. The multiple indicator electrodes (e.g., anodes) 46, 47, 48 connect to corresponding indicator cables 49, 50, 51. The indicator cables 49, 50, 51 may be fabricated from very small wires with coils to allow the indicator electrodes 46, 47, 48 to be dispersed within the soil profile 53 by the growth of the root system 54. The indicator cables 49, 50, 51 connect to acquisition module 43. The acquisition module 43 components include high-impedance potentiometer for measuring OCV between the indicator electrodes 46, 47, 48 and the cathode 41. The acquisition module 43 may incorporate a communication module allowing the data to be transmitted to an off-site user and/or a data logger.

Example 5

Figure 5:
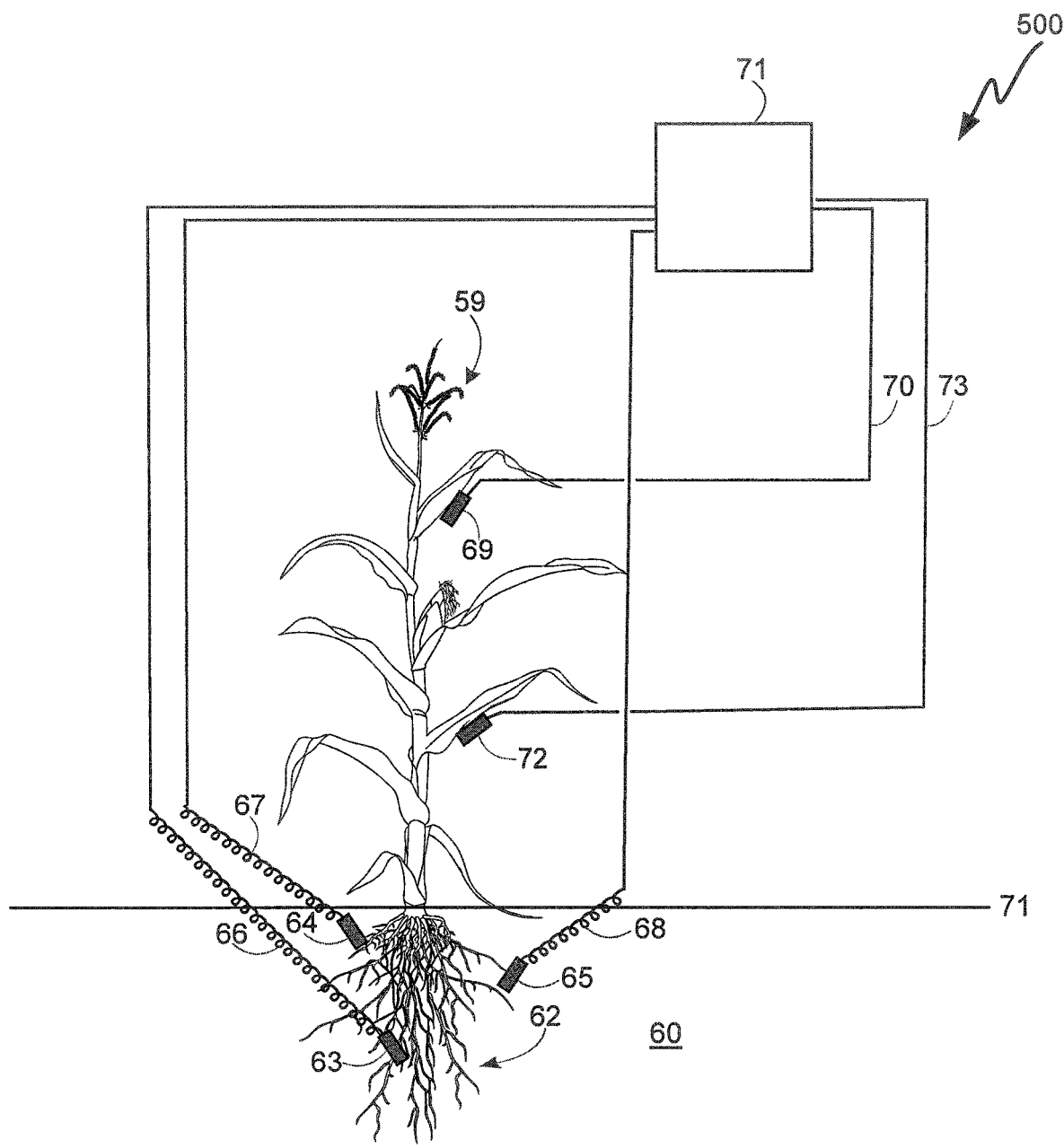
FIG. 5 illustrates a sensor system for monitoring soil conditions adjacent to a root system of a plant in accordance with at least one embodiment of the disclosure.

FIG. 5 illustrates a microbial sensing system 500 in accordance with additional embodiments of the disclosure. Microbial sensing system 500 includes a cathode 69 positioned on or embedded within a plant 59, such as the tissue of the root, stem or leaves of the plant 59. The cathode 69 connects to a cathode cable 70 that connects to an acquisition module 71.

Anodes 63, 64, 65 are placed at various vertical and horizontal locations adjacent to the roots 62 of the plant 71 to characterize the soils 60 adjacent to the root system 62.

Anodes 63, 64, 65 connect to corresponding cables 66, 67, 68. The anode cables 66, 67, 68 connect to the acquisition module 71. The acquisition module 71 may incorporate a communication module, allowing the data to be transmitted to a remote user and/or can include a data logger.

A reference cell located in the soil may be used as an alternative to the cathode 69 positioned on or with the plant 59. This alternative is described in connections with examples 1, 2 and 3.

Additionally or alternatively, an indicator electrode 72 can located on an external surface, or an internal tissue of the plant 59. The indicator electrode 72 electrically connects to an insulated cable 73. The insulated cable 73 connects to the signal acquisition module 71.

Example 6

Figure 6:
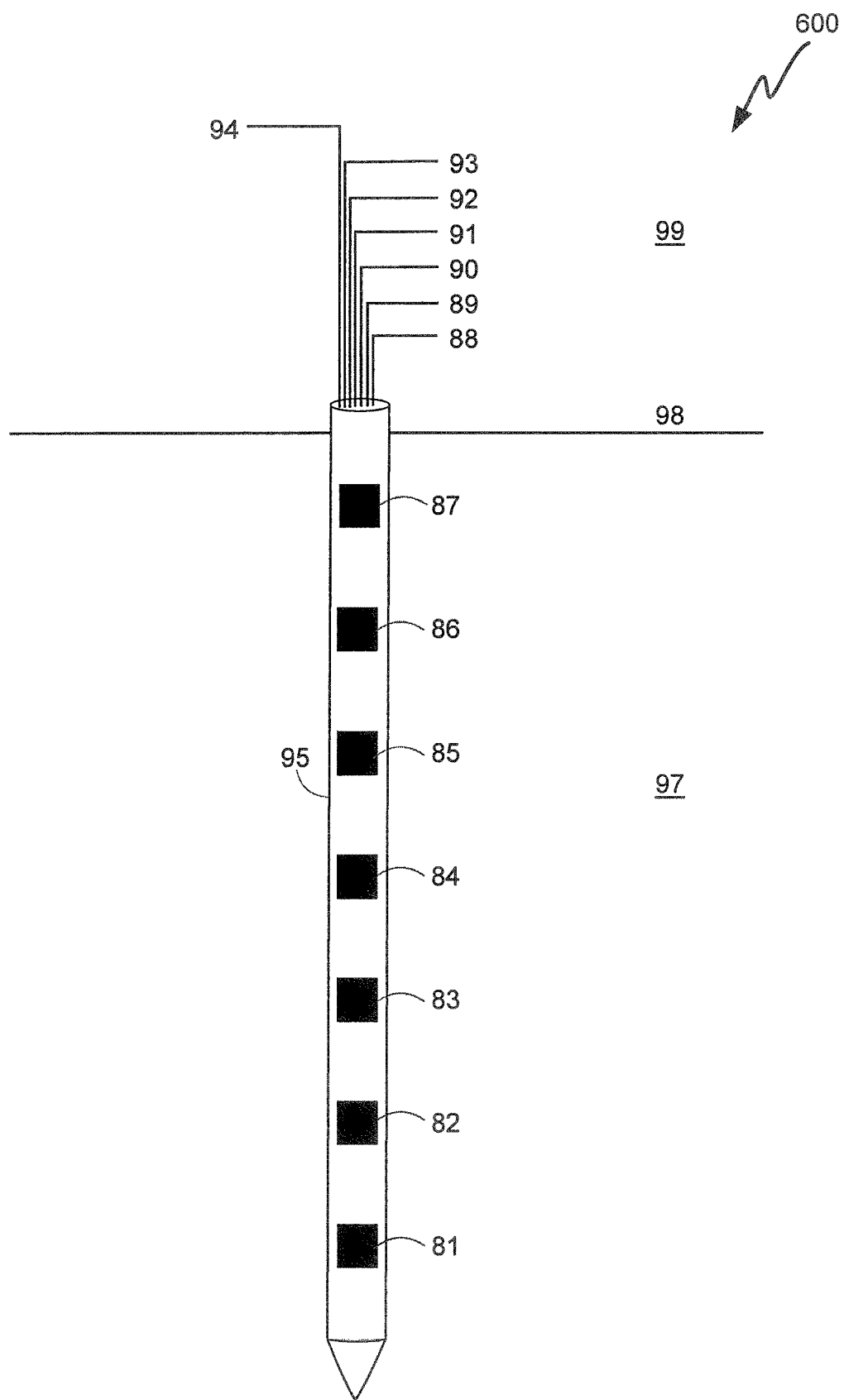
FIG. 6 illustrates a probe including microbial indicator sensors/electrodes and a reference sensor/electrode in accordance with at least one embodiment of the disclosure.

FIG. 6 illustrates a probe 600 including multiple indicator electrodes 81, 82, 83, 84, 85, 86 located along the surface a rigid substrate 95. The probe 600 can be inserted into the soil profile 97. Indicator cables 88, 89, 90, 91, 92, 93 connect to a indicator electrode 81, 82, 83, 84, 85, 86, respectively.

A cathode 87 may be incorporated within the probe 600. The cathode 87 connects to an insulated cathode cable 94. The cathode 87 can be located near the top of the probe 600—e.g., adjacent to the surface 98 of the soil profile 97. The proximity of the cathode 87 to the atmosphere 99 allows oxygen from the atmosphere 99 to be present at the surface of the cathode 87.

Example 7

Figure 7:
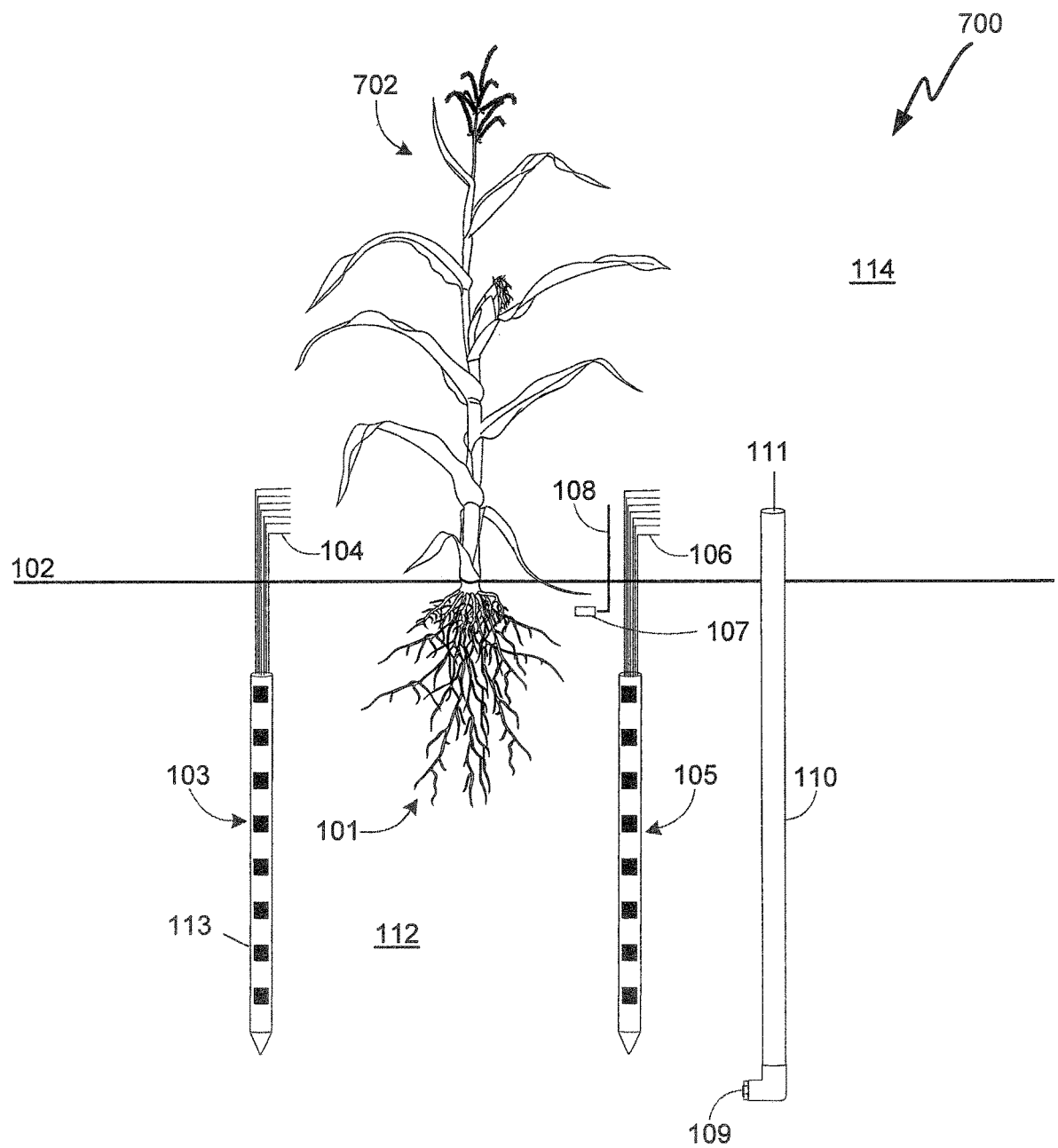
FIG. 7 illustrates a microbial sensing system with indicator sensors/electrodes incorporated in a probe and independent reference electrode in accordance with at least one embodiment of the disclosure.

FIG. 7 illustrates another microbial sensing system 700. Microbial sensing system 700 includes a microbial sensor probe 103 with multiple indicator sensors 113 and is located within a soil profile 112 adjacent to roots 101 of a plant 702. An indicator cable 104 from the microbial sensor probe 103 terminates above the surface 102 of the soil profile 112. Additional microbial probes 105 can be used to investigate the roots 101 and/or the soil profile 112. Indicator cable 106 from the microbial probe 105 can terminate above the surface 102 of the soil profile 112.

A cathode 107 with an insulated cathode cable 108 is located near or at the surface 102 of the soil profile 112. In this case, the cathode 107 can serve as the reference electrode. Alternatively, a cathode 109 can be located deeper within the soil profile 112 and a snorkel 110 can be used. An upper port 111 of the snorkel 110 is terminated within the atmosphere 114. The snorkel 110 allows oxygen within the atmosphere 114 to diffuse to the cathode 109 located in the soil profile 112.

Example 8

Figure 8:
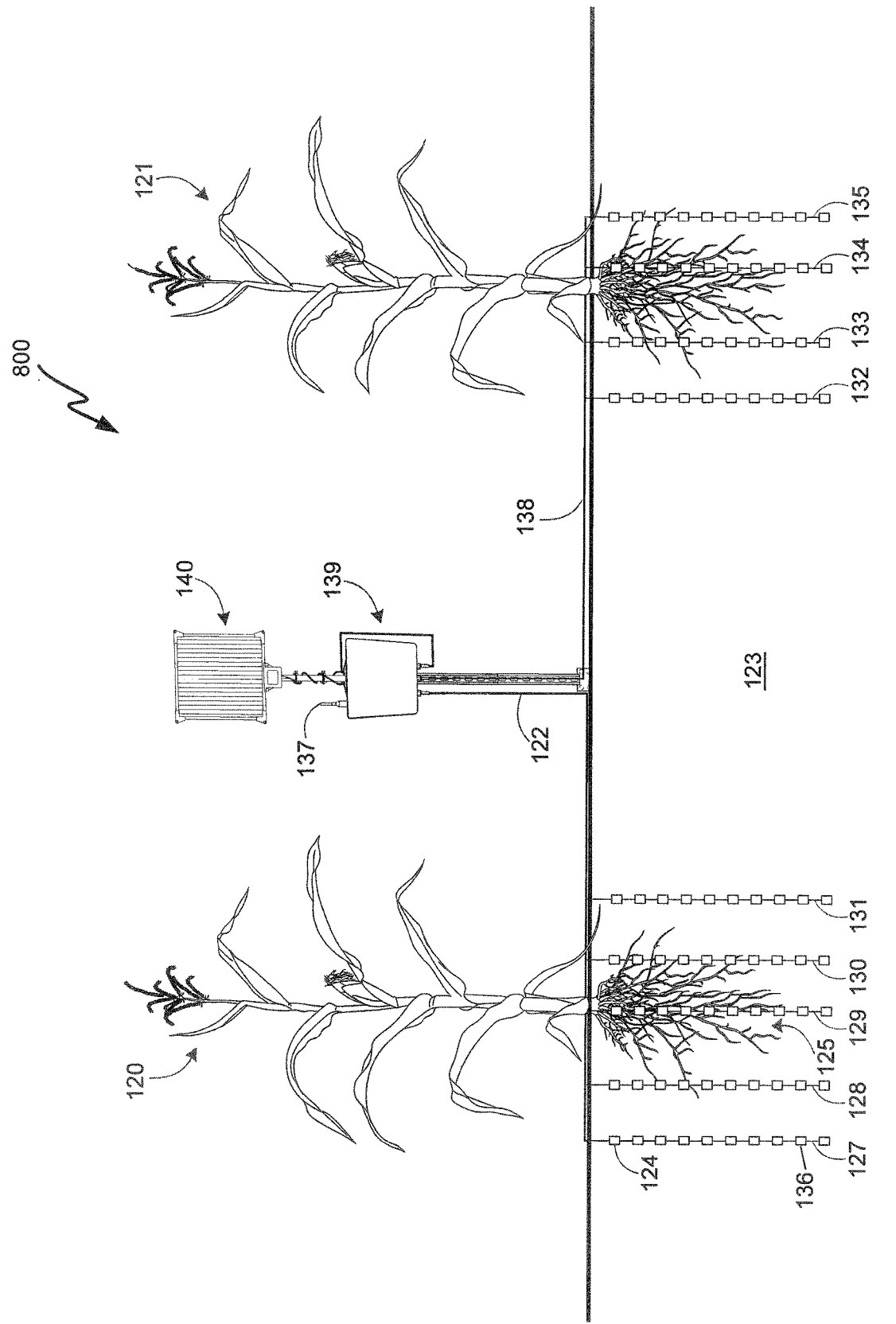
FIG. 8 illustrates microbial sensing system using multiple indicator probes located adjacent to multiple plants and a signal acquisition module for recording and/or transmitting the data in accordance with at least one embodiment of the disclosure.

FIG. 8 illustrates a microbial sensing system 800 suitable for full-scale field deployment scenarios. In this case, a root system 125 of a plant 120 and/or a soil profile 123 can be monitored by a probe 128 with multiple indicator electrodes 124, 136. Multiple probes 127, 128, 129, 130, 131 may be deployed adjacent to the root system 125 of the plant 120. Multiple plants 120, 121 can be included into the field deployment. The indicator electrodes 124, 136 in the soil probe 127 are electrically connected to an indicator cable 122. Similarly, cable 138 can be used to connect reference electrodes to signal acquisition module 139. The indicator cable 122 connects to a signal acquisition module 139. The signal acquisition module 139 includes the electrical circuitry to process the signals of the indicator electrodes 124, 136 and transmit the data to a remote device. The circuitry includes high-impedance potentiometer and electronics to create and acquire recovery voltage. The communication module, which in the illustrated example is integrated with signal acquisition module 139, can include, for example, Bluetooth®, radio telemetry, cellular and/or satellite modems. Other communication components include an antenna 137. The signal acquisition module 139 and/or the communication module can be powered by a solar cell 140. Other power options include batteries and/or a wind turbine.

The microbial sensing system 800 can programmed and operated to acquire and communicate real-time data to remote users/devices. The data is typically transmitted to cloud-based databases and the data can be downloaded with, for example, open-source dash boards and visualization programs.

Example 9

Figure 9B:
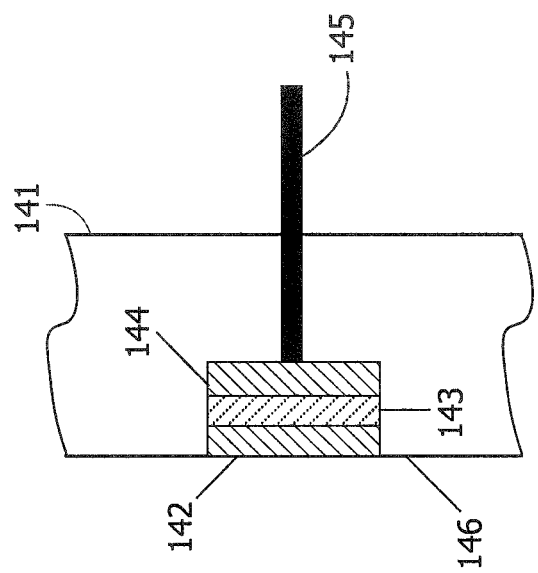
FIGS. 9A and 9B illustrate an array of electrodes in accordance with at least one embodiment of the disclosure.
Figure 9A:
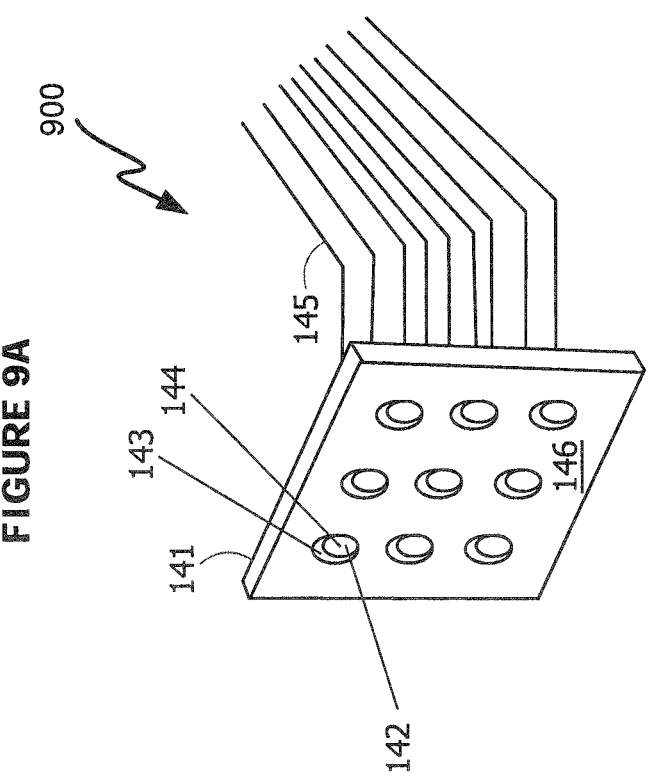

FIGS. 9A and 9B illustrate an array 900 of electrodes 144 (e.g., indicator electrodes) located on a face 146 of a polymer sensor housing 141. An insulated sensor cable 145 electrically connects to electrode 144. The microbial sensor 144 can be formed of, for example graphite, graphene, carbon fabric, or non-oxidizing material or metal (e.g., Au, Pt, Ti). The surface of the microbial sensor 144 can be covered with a nutrient (e.g., agar) and/or chemical coating 143. The nutrient and/or chemical coating 143 can become populated with a biofilm 142. The nutrient and/or chemical coating 143 can be selected to encourage the growth of different biofilms 142. Multiple electrodes can be fabricated on to the face 146 of the polymer sensor housing 141. A reference electrode can separate from array 900.

Example 10

Figure 10B:
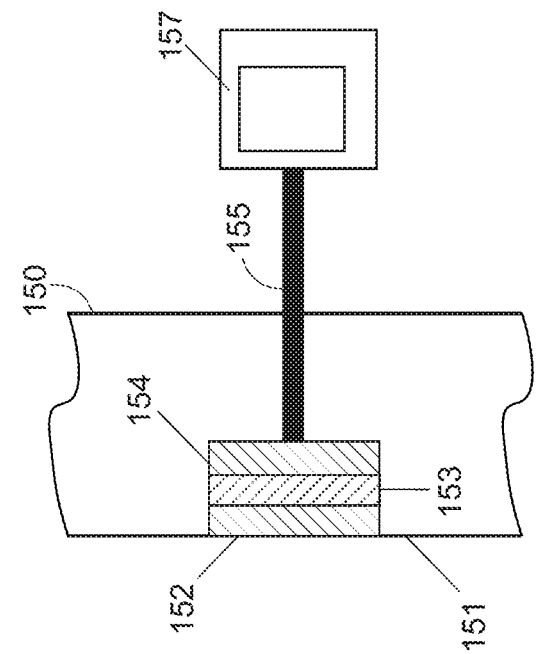
FIGS. 10A and 10B illustrate an array of electrodes and an embedded signal acquisition module and communication module in accordance with at least one embodiment of the disclosure.
Figure 10A:
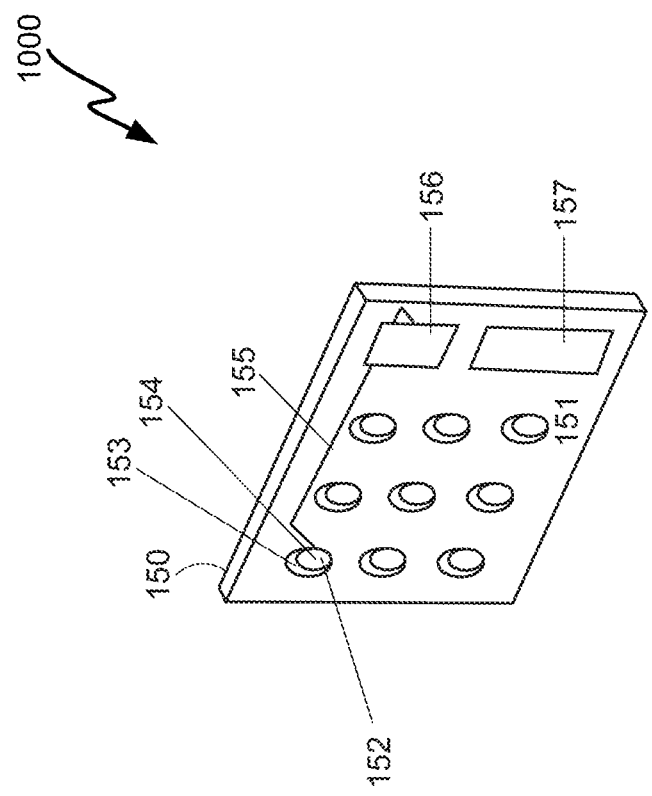

FIGS. 10A and 10B illustrate an array of electrodes 1000 that includes electrodes 154 located on a face 151 of a polymer sensor housing 150. A sensor cable 155 electrically connects to the electrode 154. The electrode 154 can fabricated of, for example, graphite, graphene, carbon fabric, or non-oxidizing material or metal (e.g., Au, Pt, Ti). The surface of the electrode 154 can be covered with a nutrient and/or chemical coating 153. The nutrient or chemical coating 153 can become populated with a biofilm 152. The nutrient or chemical coating 153 can be selected to encourage different biofilms 152. As illustrated, multiple electrodes 154 can be fabricated on to the face 151 of the polymer sensor housing 150.

The sensor cable 155 connects the electrode 154 with a signal acquisition module 156 to process the electrical signal. The signal acquisition module 156 includes a high-impedance potentiometer and circuitry to create and process a recovery voltage. The electrical signal is passed from the signal acquisition module 156 to a communication module 157. The communication module 157 transmits the electrical signal to a remote user device using, for example, Bluetooth®, radio telemetry or cellular communications. Additionally or alternatively, the communication module 157 can serve as a data logger.

It will be understood by those of skill in the art that numerous and various modifications can be made without departing from the spirit of the present invention. Therefore, it should be clearly understood that the forms of the present invention are illustrative only and are not intended to limit the scope of the present invention.

We claim:

1. A method of measuring biochemical characteristics in unsaturated soil, the method comprising the steps of:
    placing a first indicator electrode comprising inert material in a rhizosphere and within the unsaturated soil;
    placing a reference electrode in the unsaturated soil, the reference electrode comprising a second indicator electrode;
    forming a biofilm on a surface of the first indicator electrode and forming a biofilm on the second indicator electrode, wherein the biofilm on the surface of the first indicator electrode oxidizes substrates in the unsaturated soil; and
    measuring a potential difference between the first indicator electrode and the reference electrode using a high-impedance potentiometer to measure the biochemical characteristics in the unsaturated soil,
    wherein the oxidation of the substrates creates a difference in electrochemical potential between the first indicator electrode and the reference electrode,
    wherein the step of measuring the potential difference comprises measuring the difference in electrochemical potential, and
    wherein a plurality of indicator electrodes comprising the first indicator electrode and the second indicator electrode are located at vertical locations along a probe provided within the rhizosphere.

2. The method of claim 1, wherein the first indicator electrode contacts a plant.

3. The method of claim 1, further comprising a snorkel comprising an upper port that allows oxygen in an atmosphere to contact the reference electrode within the rhizosphere.

4. The method of claim 1, wherein the reference electrode comprises a non-oxidizable material.

5. The method of claim 1, wherein the second indicator electrode is in a static environment.

6. The method of claim 5, wherein the static environment comprises an anaerobic soil zone.

7. The method of claim 5, wherein the static environment comprises an artificially-created constant anaerobic environment.

8. The method of claim 5, wherein the static environment comprises an area in the soil, wherein the reference electrode is exposed to oxygen.

9. The method of claim 1, further comprising a step of providing current between the first indicator electrode and the reference electrode before the step of measuring the potential difference.

10. The method of claim 1, wherein the first indicator electrode is coated with one or more of a nutrient and a chemical coating, the one or more of the nutrient and the chemical coating to become populated with the biofilm on the surface of the first indicator electrode.

11. The method of claim 1, further comprising providing a plurality of probes within the rhizosphere and within the unsaturated soil, wherein at least one of the probes comprises a plurality of indicator electrodes including the first indicator electrode and the reference electrode, and wherein each of the probes are electrically connected to a single, central signal acquisition module.

12. The method of claim 1, wherein the first indicator electrode comprises a material selected from the group consisting of graphite, gold, platinum, titanium, and carbon fabrics.

13. A method of measuring biochemical characteristics in unsaturated soil, the method comprising the steps of:
- placing a first indicator electrode comprising inert material in a rhizosphere and within the unsaturated soil;
- placing a reference electrode in the unsaturated soil, the reference electrode comprising a second indicator electrode;
- forming a biofilm on a surface of the first indicator electrode and forming a biofilm on the second indicator electrode, wherein the biofilm on the surface of the first indicator electrode oxidizes substrates in the unsaturated soil; and
- measuring a potential difference between the first indicator electrode and the reference electrode using a high-impedance potentiometer to measure the biochemical characteristics in the unsaturated soil,
- wherein the oxidation of the substrates creates a difference in electrochemical potential between the first indicator electrode and the reference electrode, wherein the step of measuring the potential difference comprises measuring the difference in electrochemical potential,
- wherein the first indicator electrode is coated with a nutrient to become populated with the biofilm on the surface of the first indicator electrode, and
- wherein a plurality of indicator electrodes comprising the first indicator electrode and the second indicator electrode are located at vertical locations along a probe provided within the rhizosphere.

14. A method of measuring biochemical characteristics in unsaturated soil, the method comprising the steps of:
- placing a first indicator electrode comprising inert material in a rhizosphere and within the unsaturated soil;
- placing a reference electrode in the unsaturated soil, the reference electrode comprising a second indicator electrode;
- forming a biofilm on a surface of the first indicator electrode and forming a biofilm on the second indicator electrode, wherein the biofilm on the surface of the first indicator electrode oxidizes substrates in the unsaturated soil; and
- measuring a potential difference between the first indicator electrode and the reference electrode using a high-impedance potentiometer to measure the biochemical characteristics in the unsaturated soil,
- wherein the oxidation of the substrates creates a difference in electrochemical potential between the first indicator electrode and the reference electrode, wherein the step of measuring the potential difference comprises measuring the difference in electrochemical potential,
- wherein the reference electrode comprises graphite, gold, platinum, titanium, or carbon fabric, and
- wherein a plurality of indicator electrodes comprising the first indicator electrode and the second indicator electrode are located at vertical locations along a probe provided within the rhizosphere.

* * * * *